United States Patent [19]

Campbell et al.

[11] Patent Number: 4,869,740

[45] Date of Patent: Sep. 26, 1989

[54] HYDROCARBON GAS PROCESSING

[75] Inventors: Roy E. Campbell; John D. Wilkinson; Hank M. Hudson, all of Midland, Tex.

[73] Assignee: Elcor Corporation, Dallas, Tex.

[21] Appl. No.: 194,822

[22] Filed: May 17, 1988

[51] Int. Cl.⁴ .............................................. F25J 3/02
[52] U.S. Cl. ........................................ 62/24; 62/32; 62/39; 62/42
[58] Field of Search .................. 62/23, 24, 32, 36, 38, 62/39, 42

[56] References Cited

U.S. PATENT DOCUMENTS

| | | | |
|---|---|---|---|
| 3,507,127 | 4/1970 | De Marco | 62/23 |
| 3,516,261 | 6/1970 | Hoffman | 62/24 |
| 3,656,311 | 4/1972 | Kaiser | 62/28 |
| 3,902,329 | 9/1975 | King, III et al. | 62/17 |
| 4,002,042 | 1/1977 | Pryor et al. | 62/28 |
| 4,004,430 | 1/1977 | Solomon et al. | 62/18 |
| 4,115,086 | 9/1978 | Jordan et al. | 62/28 |
| 4,132,604 | 1/1979 | Alexion et al. | 62/87 |
| 4,157,904 | 6/1979 | Campbell et al. | 62/27 |
| 4,171,964 | 10/1979 | Campbell et al. | 62/24 |
| 4,251,249 | 2/1981 | Gulsby | 62/28 |
| 4,278,457 | 7/1981 | Campbell et al. | 62/24 |
| 4,507,133 | 3/1985 | Khan et al. | 62/29 |
| 4,592,766 | 6/1966 | Kumman et al. | 62/18 |
| 4,596,588 | 6/1986 | Cook | 62/26 |
| 4,617,039 | 10/1986 | Buck | 62/26 |
| 4,657,571 | 4/1987 | Gazzi | 62/17 |
| 4,687,499 | 8/1987 | Aghili | 62/24 |
| 4,711,651 | 12/1987 | Sharma et al. | 62/23 |

FOREIGN PATENT DOCUMENTS 1259083 9/1986 U.S.S.R. .

Primary Examiner—Ronald C. Capossela
Attorney, Agent, or Firm—Brumbaugh, Graves, Donohue & Raymond

[57] ABSTRACT

A process for the recovery of ethane and heavier hydrocarbon components from a hydrocarbon gas stream is disclosed. The stream is divided into first and second streams. The first stream is cooled to condense substantially all of it and is thereafter expanded to a pressure below that of the distillation column. After expansion, the cooled first stream is directed in heat exchange relation with a warmer distillation stream rising from fractionation stages of the distillation column. The warmed first stream is then separated to provide a cold vapor and a liquid stream. The liquid is supplied to the column at a first mid-column feed position and the cold vapor is supplied to the column at a second mid-column feed position. The second stream is expanded to the column pressure and is then supplied to the column at a third mid-column feed position. The distillation stream is cooled by the first stream sufficiently to partially condense it. The partially condensed distillation stream is then separated to provide volatile residue gas and a reflux stream feed. The reflux stream feed is supplied to the column at a top column feed position. In instances where the second stream is expanded in a work expansion machine, any condensation formed prior to work expansion is combined either in whole or in part with the first stream prior to cooling and/or expansion, or supplied either in whole or in part to the column as a condensed stream at a fourth mid-column feed position, or some combination thereof. The temperatures of the feeds to the column are effective to maintain the column overhead temperature at a temperature whereby the major portion of the $C_2+$ components is recovered.

35 Claims, 8 Drawing Sheets

HYDROCARBON GAS PROCESSING

BACKGROUND OF THE INVENTION

This invention relates to a process for the separation of a gas containing hydrocarbons.

Ethane, propane and heavier hydrocarbons can be recovered from a variety of gases, such as natural gas, refinery gas, and synthetic gas streams obtained from other hydrocarbon materials such as coal, crude oil, naphtha, oil shale, tar sands, and lignite. Natural gas usually has a major proportion of methane and ethane, i.e. methane and ethane together comprise at least 50 mole percent of the gas. The gas may also contain relatively lesser amounts of heavier hydrocarbons such as propane, butanes, pentanes, and the like as well as hydrogen, nitrogen, carbon dioxide and other gases.

The present invention is generally concerned with the recovery of ethane, propane and heavier hydrocarbons from such gas streams. A typical analysis of a gas stream to be processed in accordance with this invention would be, in approximate mole percent, 92.5% methane, 4.2% ethane and other $C_2$ components, 1.3% propane and other $C_3$ components, 0.4% isobutane, 0.3% normal butane, 0.5% pentanes plus, with the balance made up of nitrogen and carbon dioxide. Sulfur containing gases are also sometimes present.

Recent fluctuations in the prices of both natural gas and its NGL constituents have reduced the incremental value of ethane and heavier components as liquid products. This has resulted in a demand for processes which can provide more efficient recoveries of these products. Available processes for separating these materials include those based upon cooling and refrigeration of the gas, oil absorption, and refrigerated oil absorption. Additionally, cryogenic processes have become popular because of the availability of economical equipment which produces power while simultaneously expanding and extracting heat from the gas being processed. Depending upon the pressure of the gas source, the richness (ethane and heavier hydrocarbons content) of the gas, and the desired end products, each of these processes or a combination thereof may be employed.

The cryogenic expansion process is now generally preferred for ethane recovery because it provides maximum simplicity with ease of start up, operating flexibility, good efficiency, safety, and good reliability. U.S. Pat. Nos. 4,157,904, 4,171,964, and 4,278,457 describe relevant processes.

In a typical cryogenic expansion recovery process, a feed gas stream under pressure is cooled by heat exchange with other streams of the process and/or external sources of refrigeration such as a propane compression-refrigeration system. As the gas is cooled, liquids may be condensed and collected in one or more separators as high-pressure liquids containing some of the desired $C_2+$ components. Depending on the richness of the gas and the amount of liquid formed, the high-pressure liquids may be expanded to a lower pressure and fractionated. The vaporization occurring during expansion of the liquid results in further cooling of the stream. Under some conditions, pre-cooling the high pressure liquid prior to the expansion may be desirable in order to further lower the temperature resulting from the expansion. The expanded stream, comprising a mixture of liquid and vapor, is fractionated in a distillation (demethanizer) column. In the column, the expansion-cooled stream(s) is (are) distilled to separate residual methane, nitrogen, and other volatile gases as overhead vapor from the desired ethane, propane, and heavier components as bottom liquid product.

If the feed gas is not totally condensed (typically it is not), the vapor remaining from the partial condensation can be split into two or more streams. One portion of the vapor is passed through a work expansion machine or engine, or expansion valve, to a lower pressure at which additional liquids are condensed as a result of further cooling of the stream. The pressure after expansion is usually the same as the pressure at which the distillation column is operated. The combined vapor-liquid phases resulting from expansion are supplied as feed to the column.

The remaining portion of the vapor is cooled to substantial condensation by heat exchange with other process streams, e.g. the cold distillation column overhead Depending on the amount of high-pressure liquid available, some or all of the high-pressure liquid may be combined with this vapor portion prior to cooling. The resulting cooled stream is then expanded through an appropriate expansion device, such as an expansion valve, to the pressure at which the demethanizer is operated. During expansion, a portion of the liquid will vaporize, resulting in cooling of the total stream. Liquids thus obtained are supplied as another feed to the demethanizer. Typically, the vapor portion of the expanded stream and the demethanizer overhead vapor combine as residual methane product gas. Alternatively, the cooled and expanded stream may be supplied to a separator to provide vapor and liquid streams. The vapor is combined with the column overhead and the liquid is supplied to the column as a top column feed.

In the ideal operation of such a separation process, the residue gas leaving the process will contain substantially all of the methane in the feed gas with essentially none of the heavier hydrocarbon components and the bottoms fraction leaving the demethanizer will contain substantially all of the heavier components with essentially no methane or lighter components. In practice, however, this ideal situation is not obtained for the reason that the conventional demethanizer is operated largely as a stripping column. The methane product of the process, therefore, typically comprises vapors leaving the top fractionation stage of the column, together with vapors not subjected to any rectification step. Considerable losses of ethane occur because the top liquid feed contains substantial quantities of ethane and heavier components, resulting in corresponding equilibrium quantities of ethane and heavier components in the vapors leaving the top fractionation stage of the demethanizer. The loss of these desirable components could be significantly reduced if the rising vapors could be brought into contact with a significant quantity of liquid (reflux), containing very little ethane and heavier components; that is, reflux capable of absorbing the ethane and heavier components from the vapors. The present invention provides the means for achieving this objective and significantly improving the recovery of the desired products.

In accordance with the present invention, it has been found that $C_2$ recoveries in excess of 99 percent can be obtained. In addition, the present invention makes possible essentially 100 percent separation of methane and lighter components from the ethane and heavier components at reduced energy requirements. The present invention, although applicable at lower pressures and warmer temperatures, is particularly advantageous when processing feed gases in the range of 600 to 1000 psia or higher under conditions requiring column overhead temperatures of −120° F. or colder.

For a better understanding of the present invention, reference is made to the following examples and drawings. Referring to the drawings:

FIG. 1 is a flow diagram of a cryogenic expansion natural gas processing plant of the prior art according to U.S. Pat. No. 4,157,904;

FIG. 2 is a flow diagram of a cryogenic expansion natural gas processing plant of an alternative prior art process according to U.S. Pat. No. 4,687,499;

In the following explanation of the above figures, tables are provided summarizing flow rates calculated for representative process conditions. In the tables appearing herein, the values for flow rates (in pound moles per hour) have been rounded to the nearest whole number for convenience. The total stream rates shown in the tables include all non-hydrocarbon components and hence are generally larger than the sum of the stream flow rates for the hydrocarbon components. Temperatures indicated are approximate values, rounded to the nearest degree It should also be noted that the process design calculations performed for the purpose of comparing the processes depicted in the figures are based on the assumption of no heat leak from (or to) the surroundings to (or from) the process. The quality of commercially available insulating materials makes this a very reasonable assumption and one that is typically made by those skilled in the art.

DESCRIPTION OF THE PRIOR ART

Figure 1:
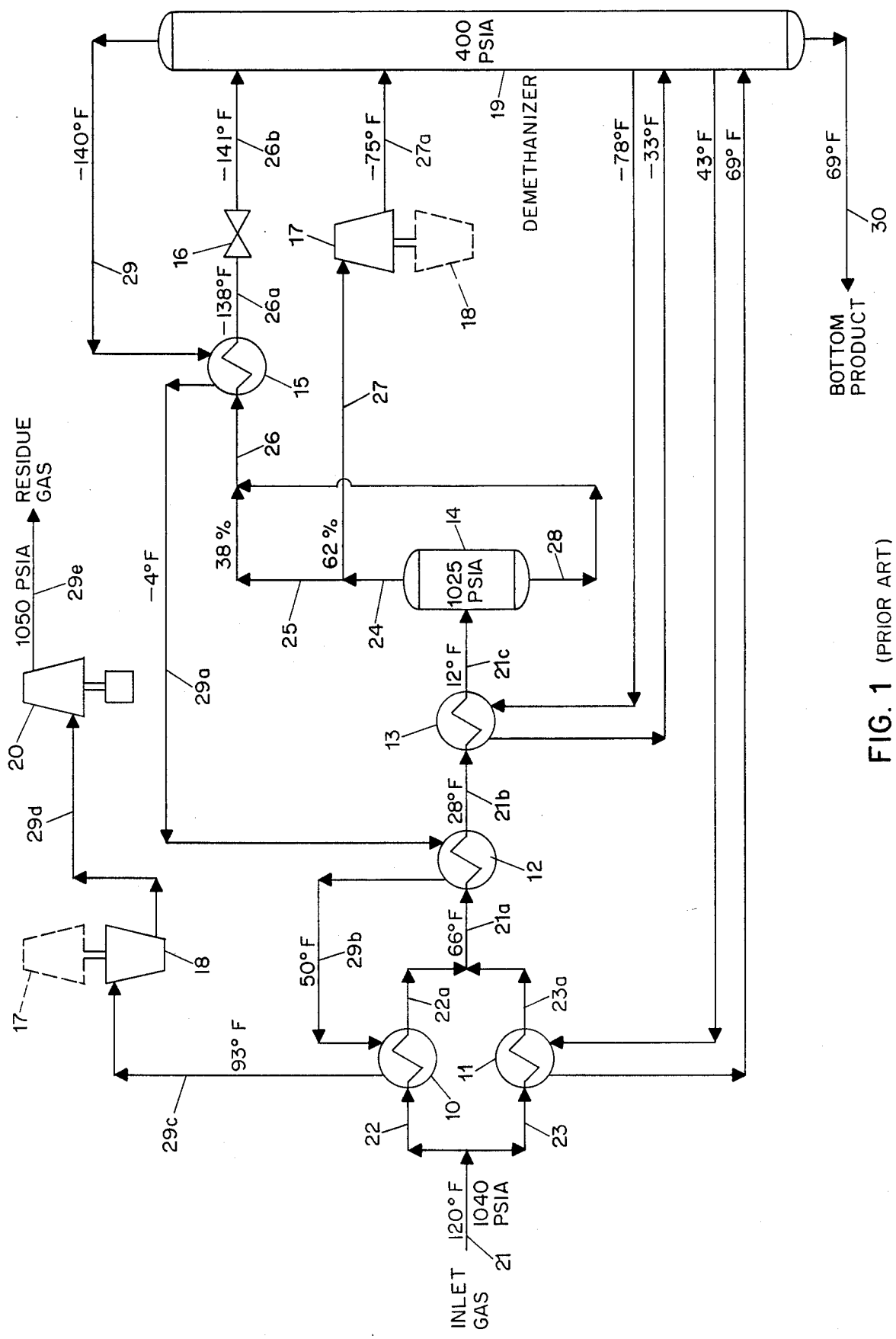

Referring now to FIG. 1, in a simulation of the process according to U.S. Pat. No. 4,157,904, inlet gas enters the plant at 120° F. and 1040 psia as stream 21. If the inlet gas contains a concentration of sulfur compounds which would prevent the product streams from meeting specifications, the sulfur compounds are removed by appropriate pretreatment of the feed gas (not illustrated). In addition, the feed stream is usually dehydrated to prevent hydrate (ice) formation under cryogenic conditions. Solid desiccant has typically been used for this purpose. The feed stream is divided into two parallel streams, 22 and 23, and cooled to 66° F. by heat exchange with cool residue gas at 50° F. in exchanger 10 and with demethanizer liquid at 43° F. in demethanizer reboiler 11. From these exchangers, streams 22a and 23a recombine as stream 21a which enters exchanger 12 where it is cooled to 28° F. (stream 21b) by cool residue gas at −4° F. (stream 29a). The feed gas continues to demethanizer side reboiler 13 and is further cooled by heat exchange with demethanizer liquid at −78° F. The further cooled stream 21c then enters separator 14 at 12° F. and 1025 psia where the vapor (stream 24) is separated from the condensed liquid (stream 28).

The vapor (stream 24) from separator 14 is divided into two streams, 25 and 27. Stream 25, containing about 38 percent of the total vapor, is combined with the separator liquid (stream 28). The combined stream 26 then passes through heat exchanger 15 in heat exchange relation with the demethanizer overhead vapor stream 29 resulting in cooling and substantial condensation of the combined stream. The substantially condensed stream 26a at −138° F. is then flash expanded through an appropriate expansion device, such as expansion valve 16, to the operating pressure (approximately 400 psia) of the distillation column, which in this instance is the demethanizing section 19b of the fractionation tower 19. During expansion a portion of the stream may vaporize, resulting in cooling of the total stream. In the process illustrated in FIG. 1, the expanded stream 26b leaving expansion valve 16 reaches a temperature of −141° F., and is supplied to the demethanizer as the top column feed.

The remaining 62 percent of the vapor from separator 14 (stream 27) enters a work expansion machine 17 in which mechanical energy is extracted from this portion of the high pressure feed. The machine 17 expands the vapor substantially isentropically from a pressure of about 1025 psia to a pressure of about 400 psia, with the work expansion cooling the expanded stream 27a to a temperature of approximately −75° F. The typical commercially available expanders are capable of recovering on the order of 80–85% of the work theoretically available in an ideal isentropic expansion. The expanded and partially condensed stream 27a is supplied as feed to the distillation column at an intermediate point.

The demethanizer in fractionation tower 19 is a conventional distillation column containing a plurality of vertically spaced trays, one or more packed beds, or some combination of trays and packing. As is often the case in natural gas processing plants, the fractionation tower consists of two sections. The upper section 19a is a separator wherein the partially vaporized top feed is divided into its respective vapor and liquid portions, and wherein the vapor rising from the lower distillation or demethanizing section is combined with the vapor portion of the top feed to form the cold residue gas stream 29 which exits the top of the tower. The lower, demethanizing section 19b contains the trays and/or packing and provides the necessary contact between the liquids falling downward and the vapors rising upward. The demethanizing section also includes reboilers which heat and vaporize a portion of the liquids flowing down the column to provide the stripping vapors which flow up the column. The bottom product stream 30 exits the bottom of the tower at 69° F., based on a typical specification of a methane to ethane ratio of 0.025:1 on a molar basis in the bottom product.

The residue 29 passes countercurrently to the incoming feed gas in: (a) heat exchanger 15 where it is heated to −4° F. (stream 29a), (b) heat exchanger 12 where it is heated to 50° F. (stream 29b), and (c) heat exchanger 10 where it is heated to 93° F. (stream 29c). The residue is then re-compressed in two stages. The first stage is compressor 18 driven by the expansion machine 17. The second stage is compressor 20 driven by a supplemental power source which compresses the residue gas to 1050 psia (stream 29e), sufficient to meet line requirements (usually on the order of the inlet pressure).

A summary of stream flow rates and energy consumption for the process illustrated in FIG. 1 is set forth in the following table:

TABLE I (FIG. 1)
Stream Flow Summary - Lb. Moles/Hr

| Stream | Methane | Ethane | Propane | Butanes+ | Total |
|---|---|---|---|---|---|
| 21 | 25381 | 1161 | 362 | 332 | 27448 |
| 24 | 25323 | 1149 | 352 | 264 | 27298 |
| 28 | 58 | 12 | 10 | 68 | 150 |
| 25 | 9752 | 443 | 136 | 102 | 10513 |
| 27 | 15571 | 706 | 216 | 162 | 16785 |
| 29 | 25355 | 118 | 7 | 1 | 25607 |
| 30 | 26 | 1043 | 355 | 331 | 1841 |
| Recoveries* | | | | | |
| Ethane | | 89.80% | | | |
| Propane | | | 98.16% | | |
| Butanes | | | | 99.53% | |
| Horsepower | | | | | |
| Residue Compression | 13,061 | | | | |

*(Based on un-rounded flow rates)

The prior art illustrated in FIG. 1 is limited to the ethane recovery shown in Table I by the equilibrium at the top of the column with the top feed to the demethanizer. Lowering the feed gas temperature at separator 14 below that shown in FIG. 1 will not increase the recovery appreciably, but will only reduce the power recovered in the expansion machine 17 and increase the residue compression horsepower correspondingly. The only way to significantly improve the ethane recovery of the prior art process of FIG. 1 is to lower the operating pressure of the demethanizer, but to do so will increase the residue compression horsepower inordinately. Even so, the ultimate ethane recovery possible will still be dictated by the composition of the top liquid feed to the demethanizer.

Figure 2:
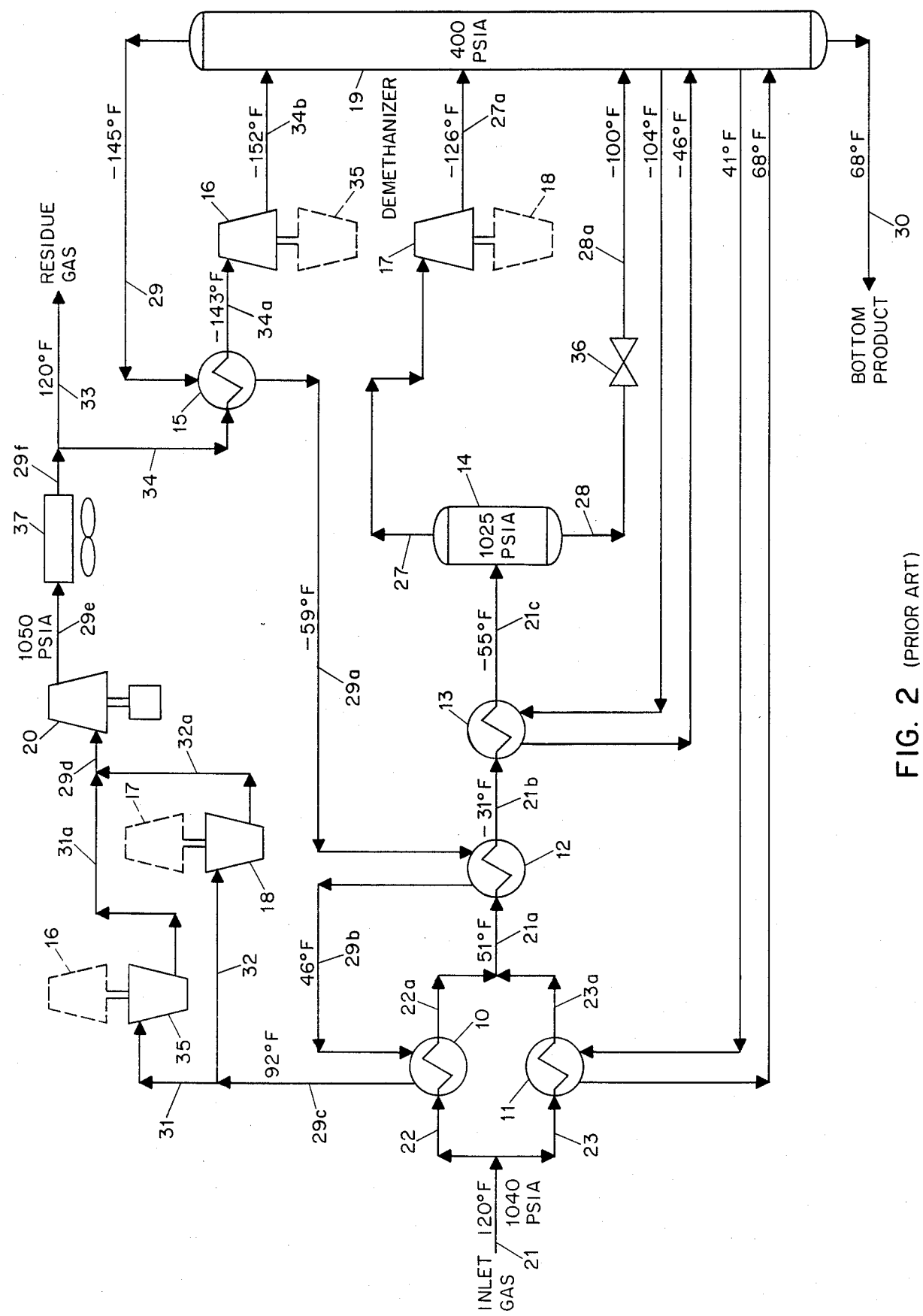

One way to achieve higher ethane recovery with the same demethanizer operating pressure is to create a leaner (lower $C_{2+}$ content) top feed. FIG. 2 represents an alternative prior art process in accordance with U.S. Pat. No. 4,687,499 that recycles a portion of the residue gas product to provide a leaner top feed to the demethanizer. The process of FIG. 2 is based on the same feed gas composition and conditions as described above for FIG. 1. In the simulation of this process operating conditions were selected to minimize energy consumption for a given recovery level. The feed stream 21 is divided into two parallel streams, 22 and 23, and cooled to 51° F. by heat exchange with cool residue gas at 46° F. in exchanger 10 and demethanizer liquid at 41° F. in demethanizer reboiler 11. From these exchangers, streams 22a and 23a recombine and stream 21a enters exchanger 12 where it is further cooled to −31° F. (stream 21b) by cool residue gas at −59° F. (stream 29a). The feed gas continues to demethanizer side reboiler 13 and is cooled by heat exchange with demethanizer liquid at −104° F. The feed stream 21c then enters separator 14 at −55° F. and a pressure of 1025 psia where the vapor (stream 27) is separated from the condensed liquid (stream 28).

The vapor from separator 14 (stream 27) enters a work expansion machine 17 in which mechanical energy is extracted from this portion of the high pressure feed. The machine 17 expands the vapor substantially isentropically from a pressure of about 1025 psia to the operating pressure of the demethanizer of about 400 psia, with the work expansion cooling the expanded stream to a temperature of approximately −126° F. The expanded and partially condensed stream 27a is supplied as feed to the demethanizer at an intermediate point. The separator liquid (stream 28) is likewise expanded to 400 psia by expansion valve 36, cooling stream 28 to −100° F. (stream 28a) before it is supplied to the demethanizer 19 a lower mid-column feed point.

A portion of the high pressure residue gas (stream 34) is withdrawn from the main residue flow (stream 29f) to become the top demethanizer feed. Recycle gas stream 34 passes through heat exchanger 15 in heat exchange relation with the cold demethanizer overhead vapor stream 29 resulting in cooling and substantial condensation of the recycle stream. The cooled stream 34a at −143° F. is then expanded through an appropriate expansion device, such as expansion machine 16, to the demethanizer operating pressure of approximately 400 psia. The machine 16 expands the stream substantially isentropically from a pressure of about 1040 psia to the demethanizer operating pressure of about 400 psia, with the work expansion cooling the expanded stream to a temperature of approximately −152° F. (stream 34b). The expanded stream 34b is supplied to the demethanizer as the top column feed.

The bottom liquid product stream 30 exits the bottom of tower 19 at 68° F. The cold residue gas stream 29 at a temperature of −145° F. passes countercurrently to the recycle gas stream in heat exchanger 15 where it is heated to −59° F. (stream 29a). The residue gas then passes countercurrently to the incoming feed gas in heat exchanger 12 where it is heated to 46° F. (stream 29b) and in heat exchanger 10 where it is heated to 92° F. (stream 29c). The residue gas is then re-compressed in two stages. Stream 29c is split into parallel streams 31 and 32 which flow to compressors 35 and 18 (driven by the expansion machines 16 and 17 respectively) for the first stage of compression. Streams 31a and 32a recombine and stream 29d flows to the second stage of compression 20 (driven by a supplemental power source) which compresses the residue gas to the line pressure of 1050 psia (stream 29e). After stream 29e is cooled to 120° F. (stream 29f) by heat exchanger 37, the recycle stream 34 is withdrawn and the residue gas product (stream 33) flows to the sales pipeline.

A summary of stream flow rates and energy consumption for the process illustrated in FIG. 2 is set forth in the following table:

TABLE II (FIG. 2)
Stream Flow Summary - (Lb. Moles/Hr)

| Stream | Methane | Ethane | Propane | Butanes+ | Total |
|---|---|---|---|---|---|
| 21 | 25381 | 1161 | 362 | 332 | 27448 |
| 27 | 24685 | 1050 | 285 | 158 | 26380 |
| 28 | 696 | 111 | 77 | 174 | 1068 |
| 34 | 7259 | 3 | 0 | 0 | 7300 |
| 29 | 32611 | 15 | 0 | 0 | 32795 |
| 30 | 29 | 1149 | 362 | 332 | 1953 |
| 33 | 25352 | 12 | 0 | 0 | 25495 |
| Recoveries* | | | | | |
| Ethane | | 98.99% | | | |
| Propane | | | 100.00% | | |
| Butanes | | | | 100.00% | |
| Horsepower | | | | | |
| Residue Compression | 17,380 | | | | |

*(Based on un-rounded flow rates)

DESCRIPTION OF THE INVENTION

EXAMPLE 1

Figure 3:
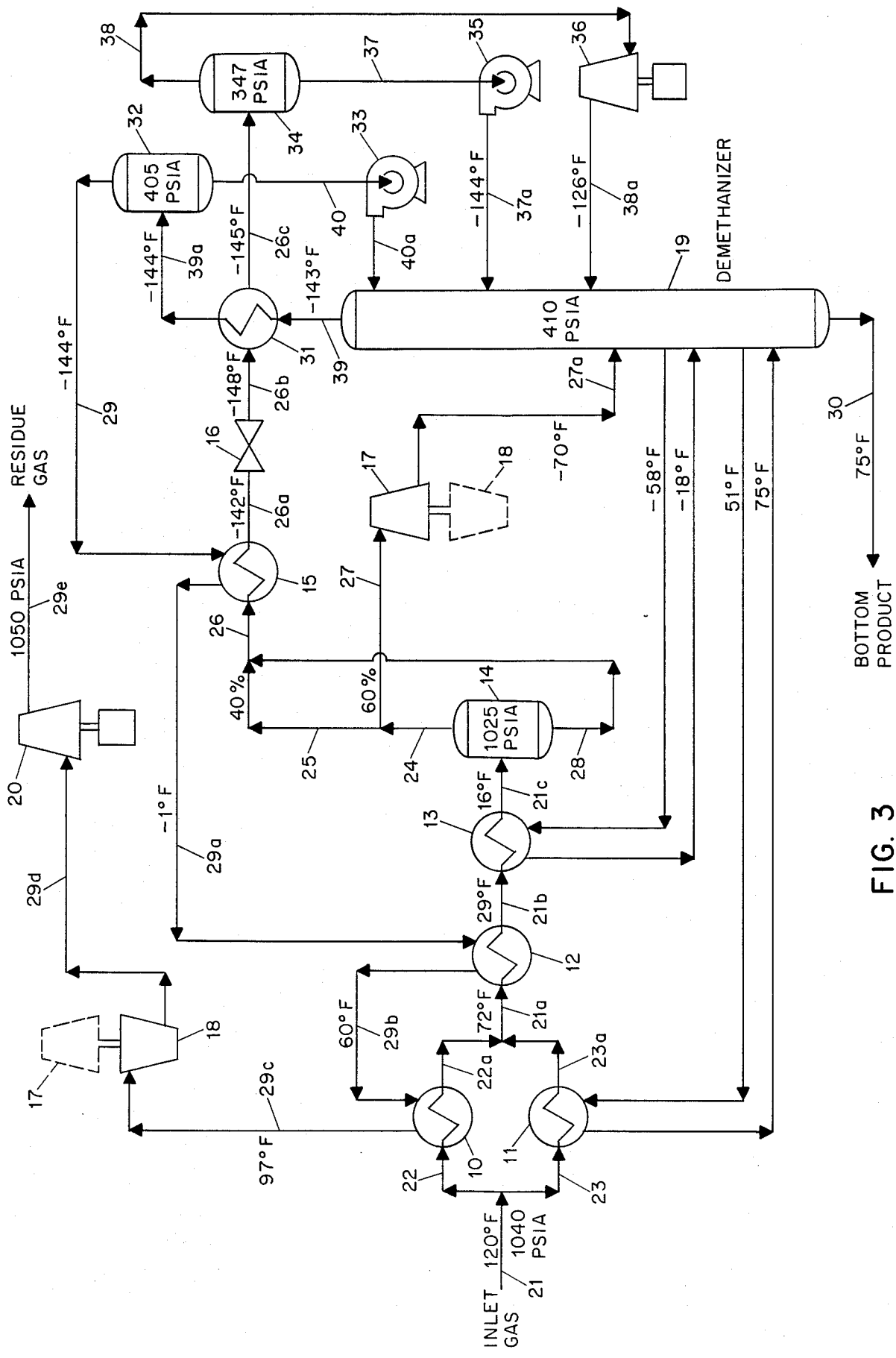
FIG. 3 is a flow diagram of a natural gas processing plant in accordance with the present invention.

FIG. 3 illustrates a flow diagram of a process in accordance with the present invention. The feed gas composition and conditions considered in the process illustrated in FIG. 3 are the same as those in FIGS. 1 and 2. Accordingly, the FIG. 3 process can be compared with the FIGS. 1 and 2 processes to illustrate the advantages of the present invention.

In the simulation of the FIG. 3 process, inlet gas enters at 120° F. and a pressure of 1040 psia as stream 21. The feed stream is divided into two parallel streams, 22 and 23, and cooled to 72° F. by heat exchange with cool residue gas at 60° F. (stream 29b) in exchanger 10 and with demethanizer liquid at 51° F. in demethanizer reboiler 11. From these exchangers, streams 22a and 23a recombine and stream 21a enters exchanger 12 where it is cooled to 29° F. (stream 21b) by cool residue gas at −1° F. (stream 29a). The further cooled stream 21b continues to demethanizer side reboiler 13 and is cooled by heat exchange with demethanizer liquid at −58° F. The feed stream 21c then enters high pressure separator 14 at 16° F. and a pressure of 1025 psia where the vapor (stream 24) is separated from condensed liquid (stream 28).

The vapor (stream 24) from separator 14 is divided into gaseous first and second streams, 25 and 27. Stream 25, containing about 40 percent of the total vapor, is combined with the separator liquid (stream 28). The combined stream 26 then passes through heat exchanger 15 in heat exchange relation with the −144° F. overhead vapor stream 29 resulting in cooling and substantial condensation of the combined stream. The substantially condensed stream 26a at −142° F. is then expanded through an appropriate expansion device, such as expansion valve 16, to a pressure of approximately 352 psia, i.e. 58 psi below the operating pressure of the distillation column 19. During expansion, a portion of the stream will vaporize, resulting in cooling of the total stream.

In the process illustrated in FIG. 3, the expanded stream 26b reaches a temperature of −148° F. and flows to the heat exchanger 31. The mixed phase stream 26b is warmed in the exchanger to −145° F. and partially vaporized as it provides cooling and partial condensation of distillation stream 39 at −143° F. flowing upward from the top-most fractionation stage of column 19. The warmed stream 26c then enters low pressure separator 34 at −145° F. and a pressure of 347 psia to provide a cold vapor stream and a liquid stream. The liquid stream 37 is pumped to demethanizer pressure by pump 35 and fed to the demethanizer at a first mid-column feed position as stream 37a at −144° F. and a pressure of 410 psia. The cold vapor stream 38 is compressed to demethanizer pressure by cold feed compressor 36 and fed to the column as stream 38a at −126° F. and a pressure of 410 psia at a second mid-column feed position.

The partially condensed distillation stream leaving exchanger 31 (stream 39a) flows to separator 32 at −144° F. and a pressure of 405 psia. The condensed liquid (stream 40) is separated and returned by means of reflux pump 33 as reflux stream 40a to column 19 at a top column feed position above the first mid-column feed position. The uncondensed vapor from separator 32 becomes residue gas stream 29 leaving the demethanizer system at −144° F.

Figure 8:
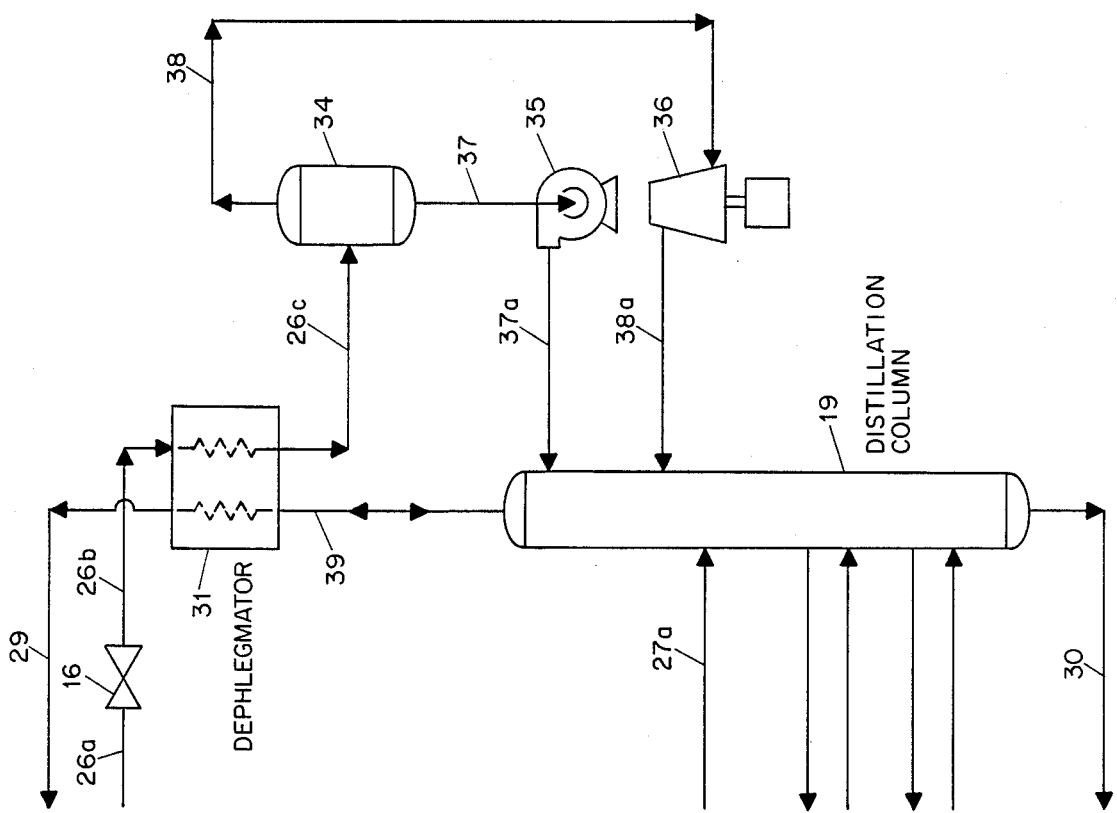
FIGS. 7 and 8 are diagrams of alternate fractionating systems which may be employed in the process of the present invention
Figure 7:
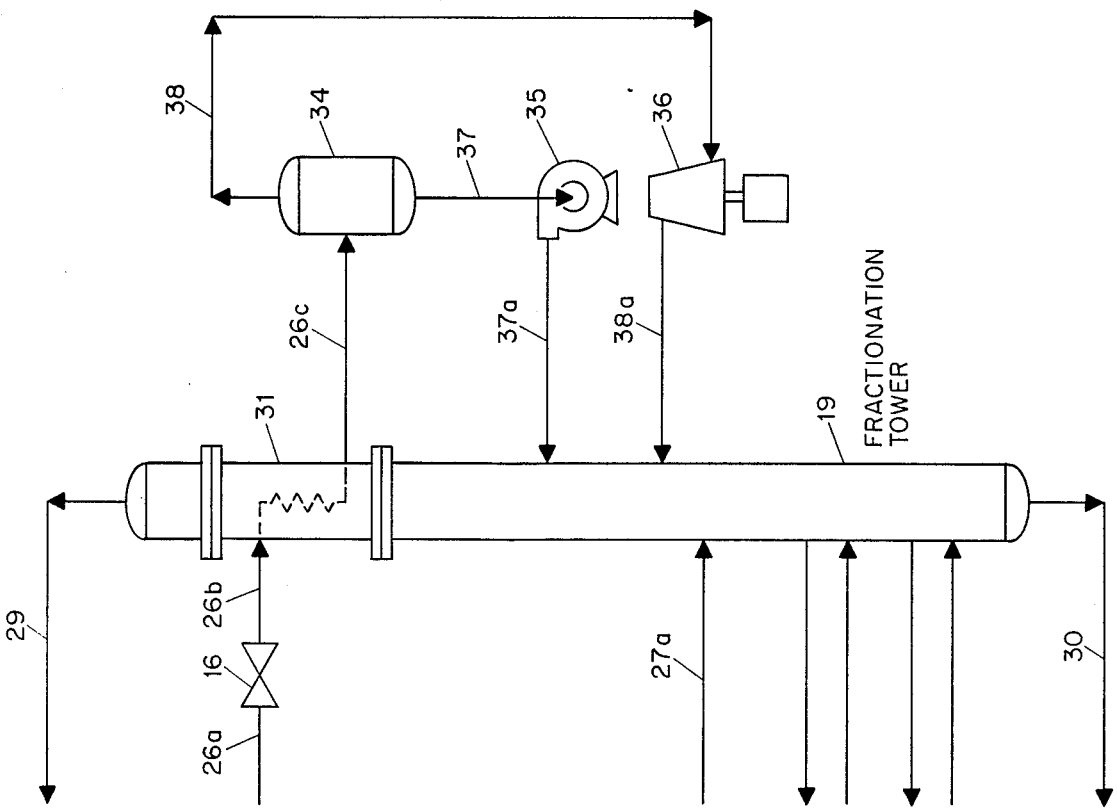

When the distillation column forms the lower portion of a fractionation tower, heat exchanger 31 may be located inside the tower above column 19 as shown in FIG. 7. This eliminates the need for separator 32 and pump 33 because the distillation stream is then both cooled and separated in the tower above the fractionation stages of the column. Alternatively and as depicted in FIG. 8, use of a dephlegmator in place of heat exchanger 31 eliminates the separator and pump and also provides concurrent fractionation stages to replace those in the upper section of the demethanizer column. If the dephlegmator is positioned in a plant at grade level, it is connected to a vapor/liquid separator and liquid collected in the separator is pumped to the top of the distillation column. The decision as to whether to include the heat exchanger inside the column or to use the dephlegmator usually depends on plant size and heat exchanger surface area requirements.

Returning to gaseous second stream 27, the remaining 60 percent of the vapor from separator 14 enters an expansion device such as work expansion machine 17 in which mechanical energy is extracted from this portion of the high pressure feed. The machine 17 expands the vapor substantially isentropically from a pressure of about 1025 psia to the pressure of the demethanizer (about 410 psia), with the work expansion cooling the expanded stream to a temperature of approximately −70° F. (stream 27a). The expanded and partially condensed stream 27a is supplied as feed to demethanizer 19 at a third mid-column feed point.

The liquid product stream 30 exits the bottom of column 19 at 75° F. The cold residue gas stream 29 passes countercurrently to stream 26 in heat exchanger 15 where it is heated to −1° F. (stream 29a) as it provides cooling and substantial condensation of stream 26. The partially warmed stream 29a then flows to heat exchanger 12 where it is further warmed to 60° F. (stream 29b) as it provides cooling of stream 21a. The further warmed residue gas stream 29b then flows to heat exchanger 10 where it is heated to 97° F. (stream 29c) as it provides cooling of inlet gas stream 22. The residue gas is then re-compressed in two stages. The first stage of compression is compressor 18 driven by the expansion machine 17. The second stage of compression is compressor 20 driven by a supplemental power source which compresses the residue gas (stream 29d) to the line pressure of 1050 psia.

A summary of stream flow rates and energy consumption for the process illustrated in FIG. 3 is set forth in the following table:

TABLE III (FIG. 3)
Stream Flow Summary - (Lb. Moles/Hr)

| Stream | Methane | Ethane | Propane | Butanes+ | Total |
|---|---|---|---|---|---|
| 21 | 25381 | 1161 | 362 | 332 | 27448 |
| 24 | 25330 | 1151 | 353 | 269 | 2731 4 |
| 28 | 51 | 10 | 9 | 63 | 134 |
| 25 | 10092 | 459 | 141 | 107 | 10883 |
| 27 | 15238 | 692 | 212 | 162 | 16431 |
| 38 | 5002 | 30 | 1 | 0 | 5067 |
| 37 | 5141 | 439 | 149 | 170 | 5950 |
| 29 | 25352 | 11 | 0 | 0 | 25532 |
| 30 | 29 | 1150 | 362 | 332 | 1916 |

| Recoveries* | |
|---|---|
| Ethane | 99.01% |
| Propane | 100.00% |
| Butanes | 100.00% |
| Horsepower | |
| Residue Compression | 13,006 |
| Cold Feed Compression | 211 |
| Cold Feed Pump | 28 |
| Reflux Pump | 23 |
| Total Horsepower | 13,268 |

*(Based on un-rounded flow rates)

By expansion of stream 26a in FIG. 3 to a pressure below that of the demethanizer, the resulting temperature of stream 26b is sufficiently below the temperature of distillation stream 39 that stream 26b provides the refrigeration driving force for heat exchanger 31. This partially condenses stream 39 and creates a liquid stream 40 that can be used to reflux the demethanizer. The reflux stream 40 contains very little ethane and heavier components, and so rectifies the vapors stripped from the feeds in the lower portions of the column thereby reducing the equilibrium vapor losses of ethane and heavier components in the residue gas stream 29.

Comparison of the recovery levels displayed in Tables I and III shows that the present invention improves ethane recovery from 89.80% to 99.01%, propane recovery from 98.16% to 100.00%, and butanes recovery from 99.53% to 100.00%. Comparison of Tables I and III further shows that the improvement in yields was not simply the result of increasing the horsepower (utility) requirements. To the contrary, when the present invention is employed, as in Example 1, not only do ethane, propane, and butanes+ recoveries increase substantially over those of the prior art process, but liquid recovery efficiency also increases by 8.5 percent (in terms of ethane recovered per unit of horsepower expended).

Comparing the present invention to the prior art process displayed in FIG. 2, Tables II and III show that the FIG. 2 prior art process essentially matches the recovery levels of the present invention for $C_2+$ components. However, the FIG. 2 process does so at the expense of greatly increased horsepower (utility) consumption. The present invention achieves the same recovery levels using only 76 percent of the external power required by the FIG. 2 prior art process.

EXAMPLE 2

Figure 4:
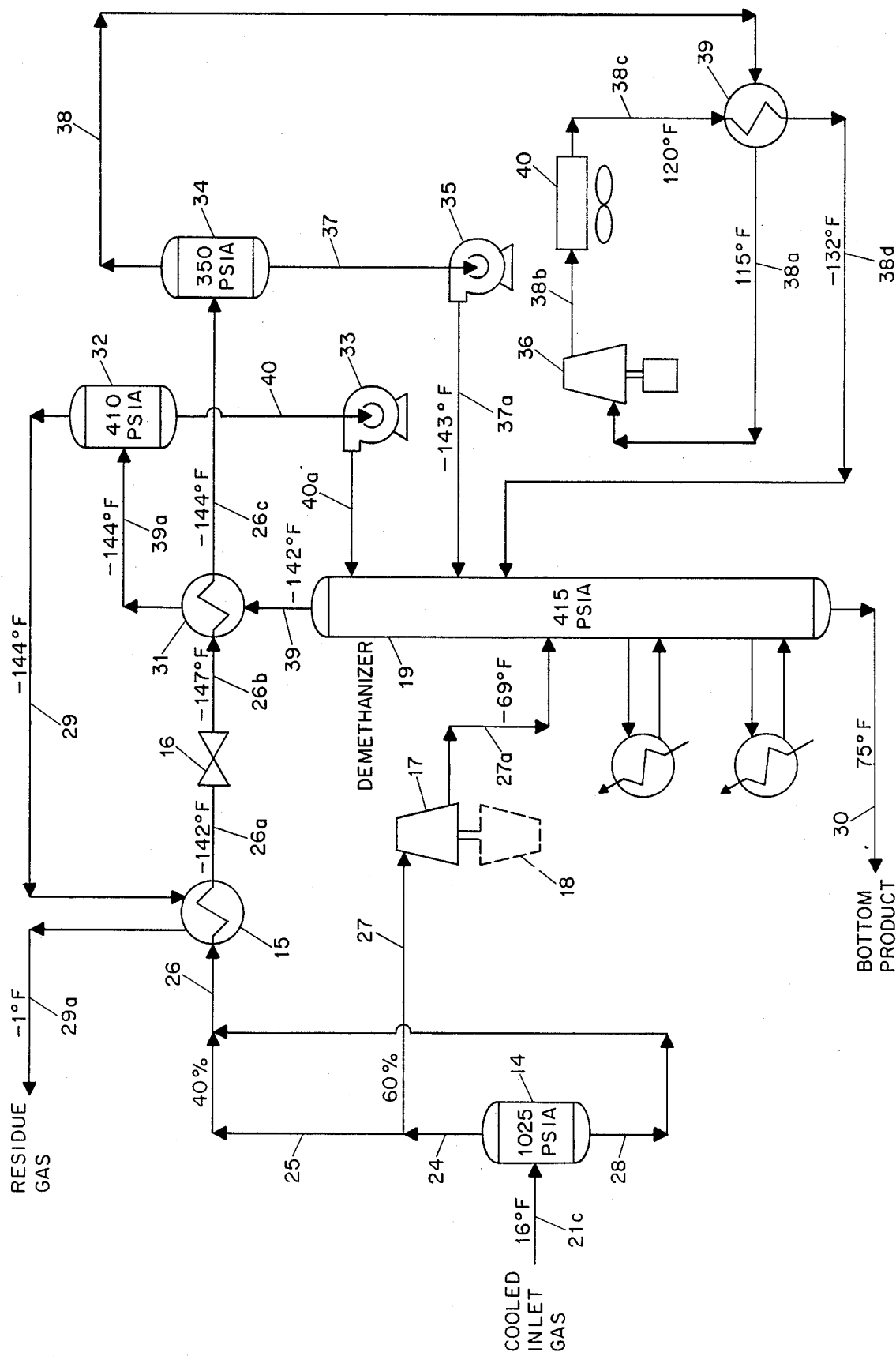
FIG. 4 is a fragmentary flow diagram illustrating an alternative means of application of the present invention to a natural gas stream.

FIG. 3 represents the preferred embodiment of the present invention for the temperature and pressure conditions shown. Another embodiment of the present invention is illustrated in the fragmentary process flow diagram shown in FIG. 4 In the simulation of the process depicted in FIG. 4, the inlet gas cooling scheme is identical to that used in FIG. 3. The difference lies in the disposition of the cold vapor (stream 38) leaving the low pressure separator 34. Rather than compressing the cold stream directly into distillation column 19, the stream can first be warmed so that cryogenic metallurgy is not required in the compressor. One method of accomplishing this is as shown in FIG. 4, where the vapor stream 38 enters cross exchanger 39 and is heated to 115° F. by heat exchange with the warm feed compressor discharge stream 38c. The warm stream 38a enters the warm feed compressor 36 and is compressed to 425 psia (stream 38b). The compressed stream is then cooled to 120° F. in heat exchanger 40. After the cross exchange with the cool stream 38, stream 38d at −132° F. enters column 19 at the second mid-column feed point.

A summary of stream flow rates and energy consumption for the process illustrated in FIG. 4 is set forth in the following table:

TABLE IV (FIG. 4)
Stream Flow Summary - (Lb. Moles/Hr)

| Stream | Methane | Ethane | Propane | Butanes+ | Total |
|---|---|---|---|---|---|
| 21c | 25381 | 1161 | 362 | 332 | 27448 |

TABLE IV-continued (FIG. 4)
Stream Flow Summary - (Lb. Moles/Hr)

| Stream | Methane | Ethane | Propane | Butanes+ | Total |
|---|---|---|---|---|---|
| 24 | 25330 | 1151 | 353 | 269 | 27314 |
| 28 | 51 | 10 | 9 | 63 | 134 |
| 25 | 10092 | 459 | 141 | 107 | 10883 |
| 27 | 15238 | 692 | 212 | 162 | 16431 |
| 38 | 5020 | 31 | 1 | 0 | 5086 |
| 37 | 5123 | 438 | 149 | 170 | 5931 |
| 29 | 25352 | 11 | 0 | 0 | 25526 |
| 30 | 29 | 1150 | 362 | 332 | 1922 |

| Recoveries* | |
|---|---|
| Ethane | 99.01% |
| Propane | 100.00% |
| Butanes | 100.00% |

| Horsepower | |
|---|---|
| Residue Compression | 12,752 |
| Warm Feed Compression | 671 |
| Cold Feed Pump | 28 |
| Reflux Pump | 23 |
| Total Horsepower | 13,474 |

*(Based on un-rounded flow rates)

A comparison of Tables III and IV shows that the FIG. 4 embodiment of the present invention can maintain high recovery levels with a slight increase in the horsepower (utility) requirements. The choice between compressing stream 38 cold or warm depends on factors such as plant size and available equipment. Alternatively, liquid stream 37a in any of the depicted embodiments may be used (1) to cool the compressed cold vapor stream or (2) to cool either the first stream or the combined stream prior to expansion and heat exchange with the distillation stream.

The process of the present invention affords the most efficient way to achieve high $C_2+$ recoveries. Alternatively, the process of the invention can be operated to attain less than maximum recoveries. If this is desired, the pressure in the separator 34 is raised, thus reducing the pressure difference between separator 34 and distillation column 19 in FIG. 3. As this pressure difference is reduced, less cooling and condensation of the distillation stream 39 occurs, resulting in less reflux liquid (stream 40a) for the column and a warmer column overhead temperature. Ethane recovery then decreases. If ethane rejection and maximum $C_3+$ recovery for a particular level of $C_2$ rejection are desired, use of the process of our co-pending application Ser. No. 194,878 is recommended.

The high pressure liquid stream 28 in FIGS. 3 and 4 need not be combined with the portion of the separator vapor (stream 25) flowing to exchanger 15. Alternatively, stream 28 (or a portion thereof) may be expanded through an appropriate expansion device, such as an expansion valve or expansion machine, and fed to a fourth mid-column feed point on distillation column 19. Stream 28 may also be used for inlet gas cooling or other heat exchange service before or after the expansion step prior to flowing to the demethanizer.

Figure 9:
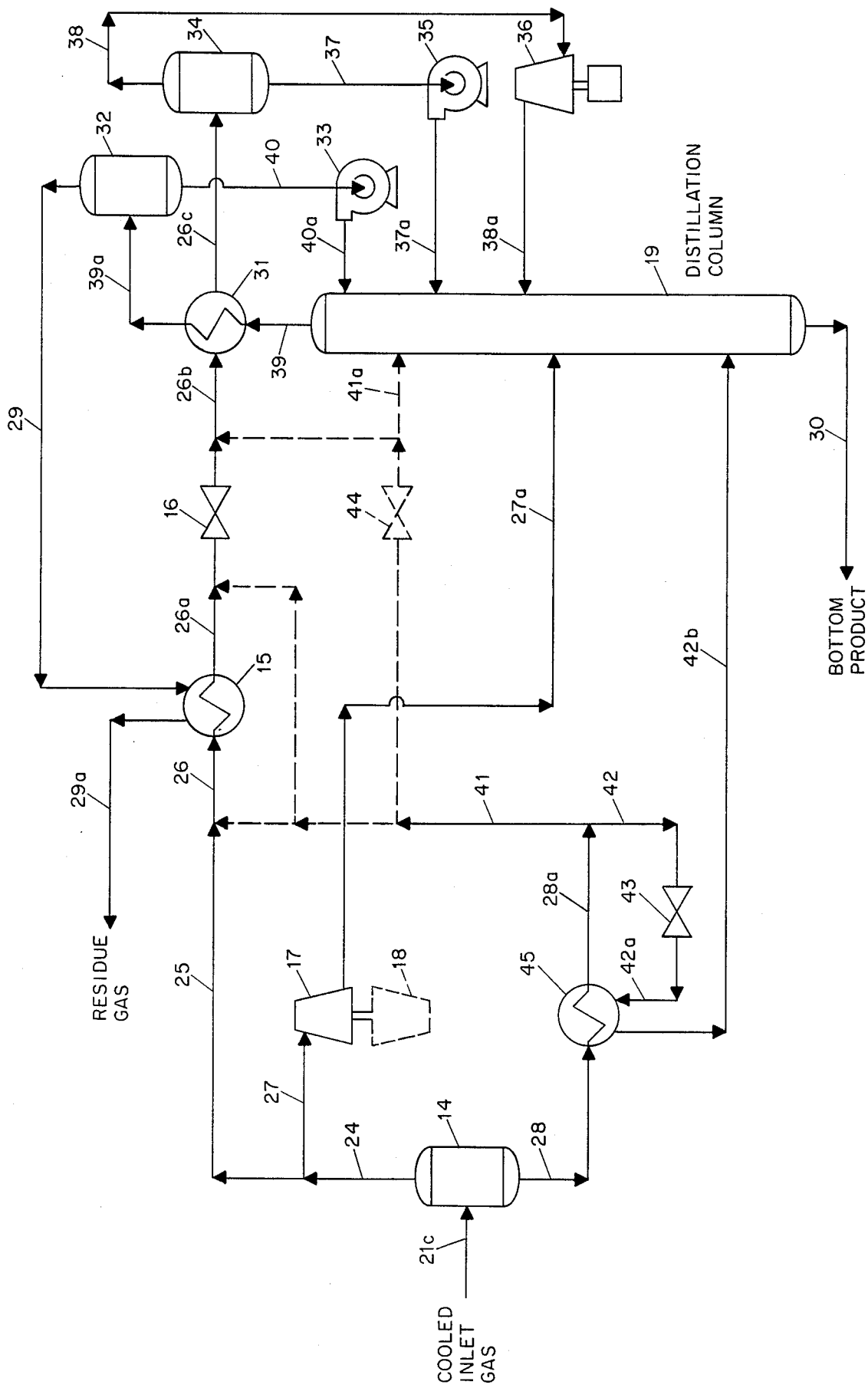
FIG. 9 is a partial flow diagram showing a natural gas processing plant in accordance with the present invention for a richer gas stream.

In instances where the inlet gas is richer than that heretofore described, an embodiment such as that depicted in FIG. 9 may be employed. Condensed stream 28 flows through exchanger 45 where it is subcooled by heat exchange with the cooled stream 42a from expansion valve 43. The subcooled liquid is then divided into two portions. The first portion flows through expansion valve 43 where it undergoes expansion and flash vaporization as the pressure is reduced to about the pressure of the distillation column. The cold stream 42a from expansion valve 43 then flows through exchanger 45 where it is used to subcool the liquids from separator 14. From exchanger 45 the stream 42b flows to distillation column 19 as a lower mid-column feed. The second liquid portion 41, still at high pressure, is (1) combined with portion 25 of the vapor stream from separator 14 or (2) combined with substantially condensed stream 26a or (3) expanded in expansion valve 44 and thereafter either supplied to the distillation column 19 at an upper mid-column feed position or combined with expanded stream 26b. Alternatively, portions of stream 41 may follow any or all of the flow paths heretofore described and depicted in FIG. 9.

Figure 5:
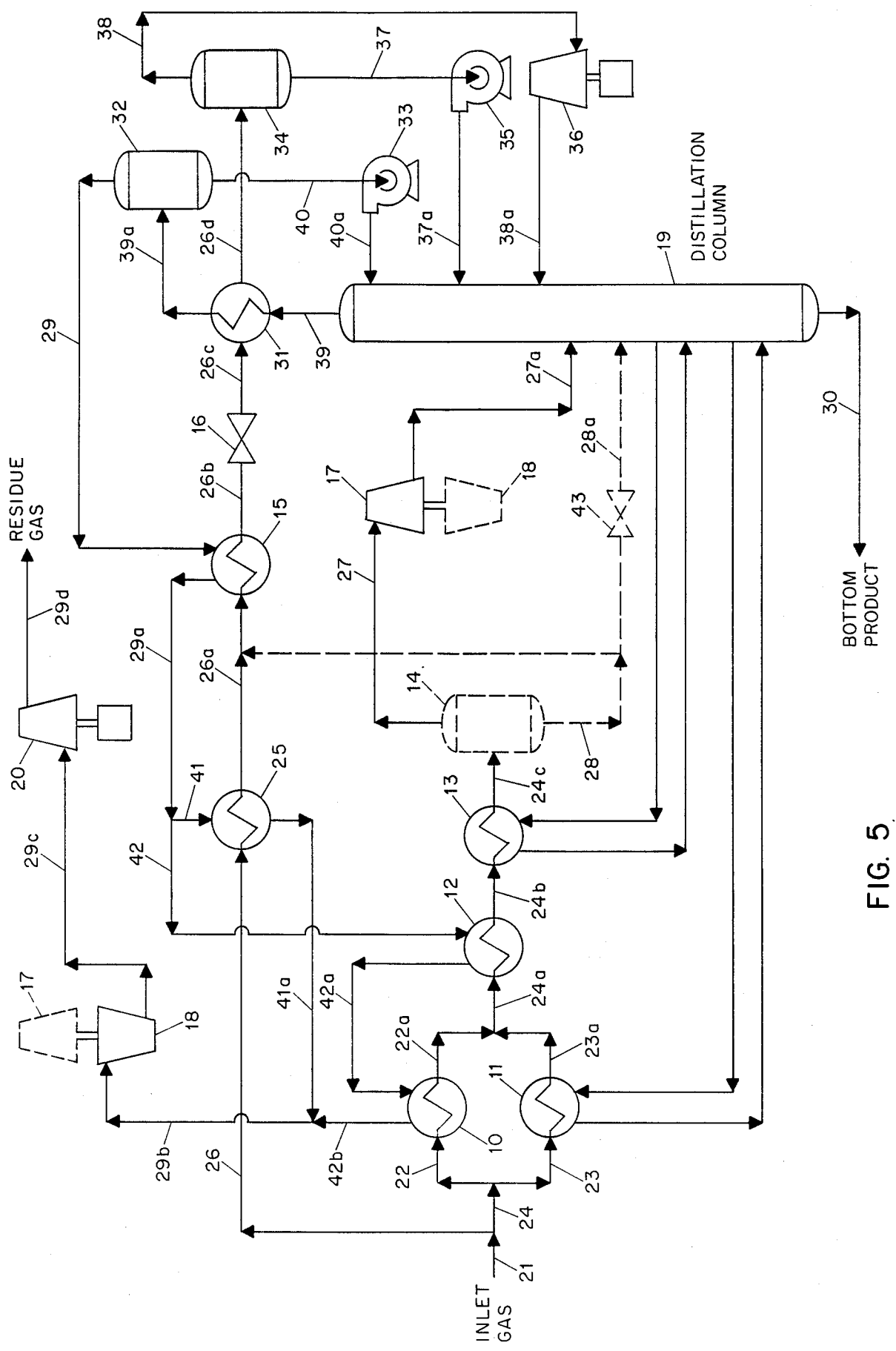
FIGS. 5 and 6 are flow diagrams of additional natural gas processing plants in accordance with the present invention.
Figure 6:
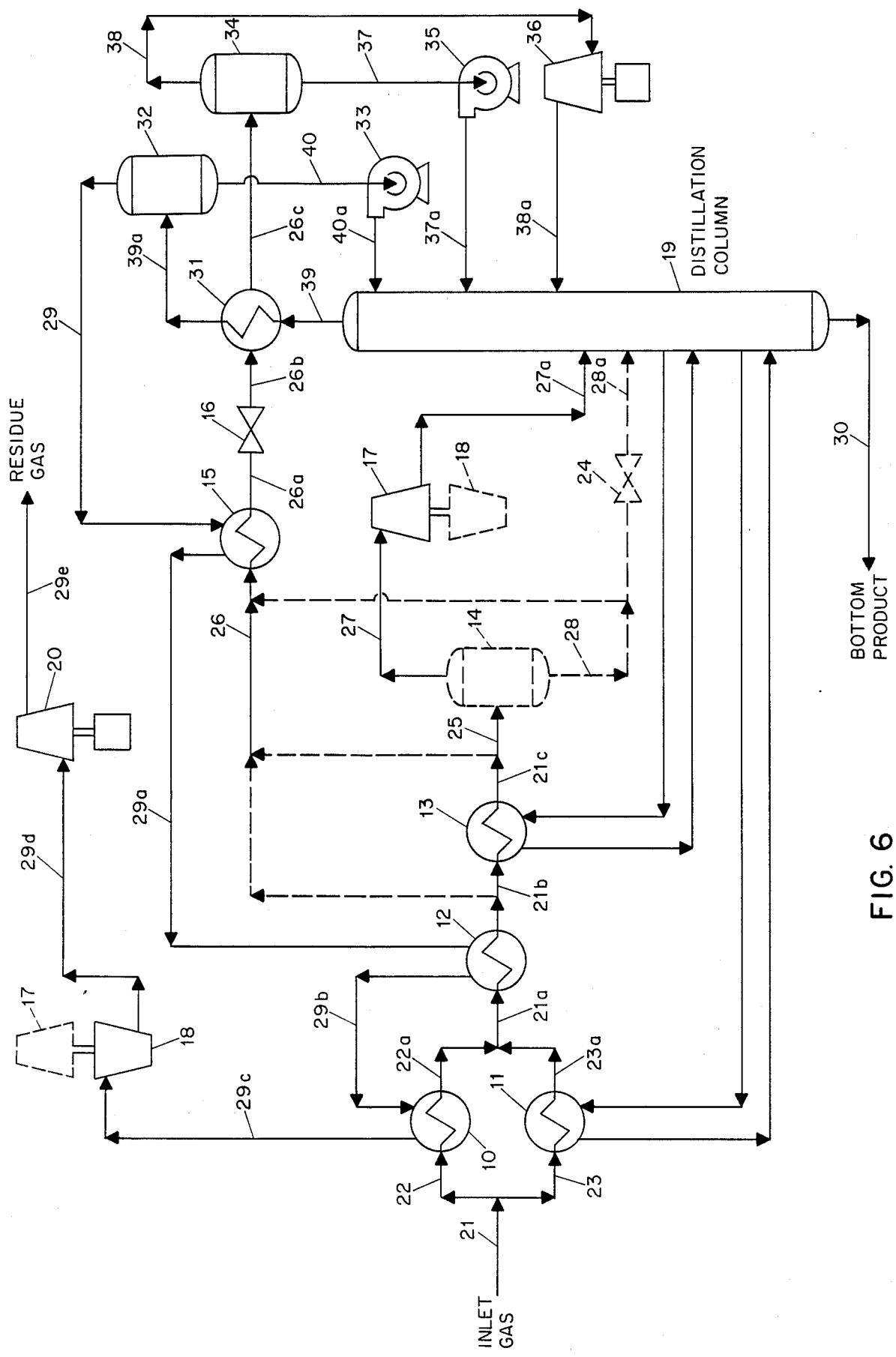

In accordance with this invention, the splitting of the vapor feed may be accomplished in several ways. In the processes of FIGS. 3 and 4, the splitting of the vapor occurs following cooling and separation of any liquids which may have been formed. The high pressure gas may be split, however, prior to any cooling of the inlet gas as shown in FIG. 5 or after the cooling of the gas and prior to any separation stages as shown in FIG. 6. In some embodiments, vapor splitting may be effected in a separator. Alternatively, the separator 14 in the processes shown in FIGS. 5 and 6 may be unnecessary if the inlet gas is relatively lean. Moreover, the use of external refrigeration to supplement the cooling available to the inlet gas from other process streams may be employed, particularly in the case of an inlet gas richer than that used in Example 1. The use and distribution of demethanizer liquids for process heat exchange, and the particular arrangement of heat exchangers for inlet gas cooling must also be evaluated for each particular application, as well as the choice of process streams for specific heat exchange services. For example, the second stream 25 depicted in FIG. 6 may be cooled after division of the inlet stream and prior to expansion of the second stream.

It will also be recognized that the relative amount of feed found in each branch of the split vapor feed will depend on several factors, including feed gas pressure, feed gas composition, the amount of heat which can economically be extracted from the feed and the quantity of horsepower available. More feed to the top of the column may increase recovery while decreasing power recovered from the expander thereby increasing the recompression horsepower requirements. Increasing feed lower in the column reduces the horsepower consumption but may also reduce product recovery. The mid-column feed positions depicted in FIGS. 3-8 are the preferred feed locations for the process operating conditions described. However, the relative locations of the mid-column feeds may vary depending on inlet composition and other factors such as desired recovery levels and amount of liquid formed during inlet gas cooling. Moreover, two or more of the feed streams, or portions thereof, may be combined depending on the relative temperatures and quantities of the individual streams, and the combined stream then fed to a mid-column feed position. FIGS. 3 and 4 are the preferred embodiments for the compositions and pressure conditions shown. Although individual stream expansion is depicted in particular expansion devices, alternative expansion means may be employed where appropriate. For example, conditions may warrant work expansion of the minor portion of the stream.

While there have been described what are believed to be preferred embodiments of the invention, those skilled in the art will recognize that other and further modifications may be made thereto e.g. to adapt the invention to various conditions, types of feed, or other requirements without departing from the spirit of the present invention as defined by the following claims.

We claim:

1. In a process for the separation of a gas containing methane, $C_2$ components and heavier hydrocarbon components into a volatile residue gas fraction containing a major portion of said methane and a relatively less volatile fraction containing a major portion of said $C_2$ components and heavier components, in which process (a) said gas is cooled under pressure to provide a cooled stream;

(b) said cooled stream is expanded to a lower pressure whereby it is further cooled; and (c) said further cooled stream is fractionated at said lower pressure whereby the major portion of said $C_2$ components and heavier hydrocarbon components is recovered in said relatively less volatile fraction;

the improvement wherein said gas is cooled sufficiently to partially condense it; and (1) said partially condensed gas is separated thereby to provide a vapor stream and a condensed stream;

(2) said vapor stream is thereafter divided into gaseous first and second streams;

(3) said gaseous first stream is combined with at least a portion of said condensed stream to form a combined stream and said combined stream is cooled to condense substantially all of it and is thereafter expanded to a pressure below the fractionation pressure;

(4) the expanded cooled combined stream is then directed in heat exchange relation with a warmer distillation stream which rises from fractionation stages of a distillation column;

(5) the distillation stream is cooled by said combined stream sufficiently to partially condense it and said partially condensed distillation stream is separated thereby to provide said volatile residue gas and a reflux stream, said reflux stream is supplied to said distillation column at a top column feed position;

(6) the combined stream is separated thereby to provide a cold vapor stream and a liquid stream, the liquid stream is pumped to said column at a first mid-column feed position;

(7) the cold vapor stream is compressed and fed to the column at a second mid-column feed position;

(8) the gaseous second stream is expanded to said fractionation pressure and is supplied to said distillation column at a third mid-column feed position; and (9) the temperatures of said feeds to the column are effective to maintain column overhead temperature at a temperature whereby the major portion of said $C_2$ components and heavier hydrocarbon components is recovered in said relatively less volatile fraction.

2. The improvement according to claim 1 wherein the distillation column is a lower portion of a fractionation tower and wherein (a) the distillation stream is cooled by the expanded cooled combined stream and (b) the cooled distillation stream is separated to provide the volatile residue gas and the reflux stream in a portion of the tower above the distillation column and wherein said reflux stream flows to the top fractionation stage of the distillation column.

3. The improvement according to claim 1 wherein the reflux stream is directed through a pump to the distillation column.

4. The improvement according to claim 1 wherein the distillation stream is (a) cooled to partially condense it and (b) separated in a dephlegmator to provide said volatile residue gas and a reflux stream and wherein the reflux stream flows from the dephlegmator to the top fractionation stage of the distillation column.

5. In a process for the separation of a gas containing methane, $C_2$ components and heavier hydrocarbon components into a volatile residue gas fraction containing a major portion of said methane and a relatively less volatile fraction containing a major portion of said $C_2$ components and heavier components, in which process
   (a) said gas is cooled under pressure to provide a cooled stream;
   (b) said cooled stream is expanded to a lower pressure whereby it is further cooled; and
   (c) said further cooled stream is fractionated at said lower pressure whereby the major portion of said $C_2$ components and heavier components is recovered in said relatively less volatile fraction;
the improvement wherein prior to cooling, said gas is divided into gaseous first and second streams and
   (1) said gaseous first stream is cooled to condense substantially all of it and is thereafter expanded to a pressure below the fractionation pressure;
   (2) said gaseous second stream is cooled under pressure and is thereafter expanded to said lower pressure;
   (3) the expanded cooled first stream is directed in heat exchange relation with a warmer distillation stream which rises from fractionation stages of a distillation column;
   (4) the distillation stream is cooled by said first stream sufficiently to partially condense it and said partially condensed distillation stream is separated thereby to provide said volatile residue gas and a reflux stream, said reflux stream is supplied to said distillation column at a top column feed position;
   (5) the first stream is separated thereby to provide a cold vapor stream and a liquid stream, the liquid stream is pumped to said distillation column at a first mid-column feed position;
   (6) the cold vapor stream is compressed and fed to the column at a second mid-column feed position;
   (7) the expanded cooled second stream is supplied to said distillation column at a third mid-column feed position; and
   (8) the temperatures of said feeds to the column are effective to maintain column overhead temperature at a temperature whereby the major portion of said $C_2$ components and heavier hydrocarbon components is recovered in said relatively less volatile fraction.

6. The improvement according to claim 5 wherein the distillation column is a lower portion of a fractionation tower and wherein
   (a) the distillation stream is cooled by the expanded cooled first stream and
   (b) the cooled distillation stream is separated to provide the volatile residue gas and the reflux stream in a portion of the tower above the distillation column and wherein said reflux stream flows to the top fractionation stage of the distillation column.

7. The improvement according to claim 5 wherein the reflux stream is directed through a pump to the distillation column.

8. The improvement according to claim 5 wherein the distillation stream is (a) cooled to partially condense it and (b) separated in a dephlegmator to provide said volatile residue gas and a reflux stream and wherein the reflux stream flows from the dephlegmator to the top fractionation stage of the distillation column.

9. The improvement according to claim 5 wherein the second stream is expanded to said lower pressure in a work expansion machine and wherein
   (a) prior to work expansion, said second stream is a partially condensed stream;
   (b) said partially condensed second stream is separated thereby to provide another vapor stream and a condensed stream;
   (c) said other vapor stream is expanded in the work expansion machine and supplied to said distillation column at a second mid-column feed position; and
   (d) at least a portion of said condensed stream is combined with said first stream to form a combined stream which is cooled to condense substantially all of it and is thereafter expanded to a pressure below the fractionation pressure and wherein said expanded combined stream is then directed in heat exchange relation with said distillation stream.

10. The improvement according to claim 5 wherein the second stream is expanded to said lower pressure in a work expansion machine and wherein
    (a) prior to work expansion, said second stream is a partially condensed stream;
    (b) said partially condensed second stream is separated thereby to provide another vapor stream and a condensed stream;
    (c) said other vapor stream is expanded in the work expansion machine and supplied to said distillation column at a second mid-column feed position; and
    (d) said condensed stream is expanded to said fractionation pressure and is supplied to said distillation column at a fourth mid-column feed position.

11. In a process for the separation of a gas containing methane, $C_2$ components and heavier hydrocarbon components into a volatile residue gas fraction containing a major portion of said methane and a relatively less volatile fraction containing a major portion of said $C_2$ components and heavier components, in which process
    (a) said gas is cooled under pressure to provide a cooled stream;
    (b) said cooled stream is expanded to a lower pressure whereby it is further cooled; and
    (c) said further cooled stream is fractionated at said lower pressure whereby the major portion of said $C_2$ components and heavier hydrocarbon components is recovered in said relatively less volatile fraction;
the improvement wherein following cooling, said cooled stream is divided into first and second streams and
    (1) said first stream is cooled to condense substantially all of it and is thereafter expanded to a pressure below the fractionation pressure;
    (2) said second stream is expanded to said lower pressure;

(3) the expanded cooled first stream is directed in heat exchange relation with a warmer distillation stream which rises from fractionation stages of a distillation column;

(4) the distillation stream is cooled by said first stream sufficiently to partially condense it and said partially condensed distillation stream is separated thereby to provide said volatile residue gas and a reflux stream, said reflux stream is supplied to said distillation column at a top column feed position;

(5) the first stream is separated thereby to provide a cold vapor stream and a liquid stream, the liquid stream is pumped to said column at a first mid-column feed position;

(6) the cold vapor stream is compressed and fed to the column at a second mid-column feed position;

(7) the expanded second stream is supplied to said distillation column at a third mid-column feed position; and (8) the temperatures of said feeds to the column are effective to maintain column overhead temperature at a temperature whereby the major portion of said $C_2$ components and heavier hydrocarbon components is recovered in said relatively less volatile fraction.

12. The improvement according to claim 11 wherein the distillation column is a lower portion of a fractionation tower and wherein
   (a) the distillation stream is cooled by the expanded cooled first stream and
   (b) the cooled distillation stream is separated to provide the volatile residue gas and the reflux stream in a portion of the tower above the distillation column and wherein said reflux stream flows to the top fractionation stage of the distillation column.

13. The improvement according to claim 11 wherein the reflux stream is directed through a pump to the distillation column.

14. The improvement according to claim 11 wherein the distillation stream is (a) cooled to partially condense it and (b) separated in a dephlegmator to provide said volatile residue gas and a reflux stream and wherein the reflux stream flows from the dephlegmator to the top fractionation stage of the distillation column.

15. The improvement according to claim 11 wherein the second stream is cooled after said division and prior to the expansion to said lower pressure.

16. The improvement according to claim 11 wherein the second stream is expanded to said lower pressure in a work expansion machine and wherein
   (a) prior to work expansion, said second stream is a partially condensed stream;
   (b) said partially condensed second stream is separated thereby to provide another vapor stream and a condensed stream;
   (c) said other vapor stream is expanded in the work expansion machine and supplied to said distillation column at a second mid-column feed position; and
   (d) at least a portion of said condensed stream is combined with said first stream to form a combined stream which is cooled to condense substantially all of it and is thereafter expanded to a pressure below the fractionation pressure and wherein said expanded combined stream is then directed in heat exchange relation with said distillation stream.

17. The improvement according to claim 1, 5 or 11 wherein said cold vapor stream is cooled after compression.

18. The improvement according to claim 17 wherein said liquid stream cools said cold vapor stream after compression.

19. The improvement according to claim 1, 5 or 11 wherein the stream directed in heat exchange relation with the distillation stream is cooled prior to expansion by said liquid stream.

20. The improvement according to claim 1, 9 or 16 wherein at least a portion of the condensed stream is expanded to said lower pressure and is supplied to said distillation column at a fourth mid-column feed position.

21. The improvement according to claim 20 wherein said cold vapor stream is cooled after compression.

22. The improvement according to claim 20 wherein at least portions of at two of said liquid stream, said cold vapor stream, said second stream and said condensed stream are combined to form a second combined stream and said second combined stream is supplied to said column at a mid-column feed position.

23. The improvement according to claim 5 or 11 wherein at least portions of least two of said liquid stream, said cold vapor stream and said second stream are combined to form a combined stream and said combined stream is supplied to said column at a mid-column feed position.

24. The improvement according to claim 1, 9 or 16 wherein,
   (a) said condensed stream is cooled and divided into first and second portions;
   (b) said first portion is expanded to said lower pressure and supplied to said column at a mid-column feed position; and
   (c) the second portion is supplied to said column at a higher mid-column feed position.

25. The improvement according to claim 24 wherein
   (a) at least part of said second portion is combined with said first stream to form a combined stream and said combined stream is directed in heat exchange relation with said distillation stream and then separated to provide said cold vapor stream and said liquid stream; and
   (b) the remainder of said second portion is expanded to said lower pressure and supplied to said column at another mid-column feed position.

26. The improvement according to claim 24 wherein the first portion is expanded, directed in heat exchange relation with said condensed stream and then supplied to said column at a lower mid-column feed position.

27. The improvement according to claim 24 wherein said second portion is expanded to said lower pressure and at least part of said expanded second portion is combined with said expanded cooled first stream to form a combined stream and said combined stream is directed in heat exchange relation with said distillation stream and then separated to provide said cold vapor stream and said liquid stream.

28. In a process for the separation of a gas containing methane, $C_2$ components and heavier hydrocarbon components into a volatile residue gas fraction containing a major portion of said methane and a relatively less volatile fraction containing a major portion of said $C_2$ components and heavier components, in which process
   (a) said gas is cooled under pressure to provide a cooled stream;

(b) said cooled stream is expanded to a lower pressure whereby it is further cooled; and (c) said further cooled stream is fractionated at said lower pressure whereby the major portion of said $C_2$ components and heavier hydrocarbon components is recovered in said relatively less volatile fraction;

the improvement wherein said gas is cooled sufficiently to partially condense it; and (1) said partially condensed gas is separated thereby to provide a vapor stream and a condensed stream;

(2) said vapor stream is thereafter divided into gaseous first and second streams;

(3) said gaseous first stream is cooled to condense substantially all of it and is thereafter expanded to a pressure below the fractionation pressure;

(4) the expanded cooled first stream is then directed in heat exchange relation with a warmer distillation stream which rises from fractionation stages of a distillation column;

(5) the distillation stream is cooled by said first stream sufficiently to partially condense it and said partially condensed distillation stream is separated thereby to provide said volatile residue gas and a reflux stream, said reflux stream is supplied to said distillation column at a top column feed position;

(6) the first stream is separated thereby to provide a cold vapor stream and a liquid stream, the liquid stream is pumped to said column at a first mid-column feed position;

(7) the cold vapor stream is compressed and fed to the column at a second mid-column feed position;

(8) the gaseous second stream is expanded to said fractionation pressure and is supplied to said distillation column at a third mid-column feed position;

(9) said condensed stream is expanded to said fractionation pressure and is supplied to said distillation column at a fourth mid-column feed position; and

(10) the temperatures of said feeds to the column are effective to maintain column overhead temperature at a temperature whereby the major portion of said $C_2$ components and heavier hydrocarbon components is recovered in said relatively less volatile fraction.

29. The improvement according to claim 11 wherein the second stream is expanded to said lower pressure in a work expansion machine and wherein (a) prior to work expansion, said second stream is a partially condensed stream;

(b) said partially condensed second stream is separated thereby to provide another vapor stream and a condensed stream;

(c) said other vapor stream is expanded in the work expansion machine and supplied to said distillation column at a second mid-column feed position; and (d) said condensed stream is expanded to said fractionation pressure and is supplied to said distillation column at a fourth mid-column feed position.

30. In an apparatus for the separation of a gas containing methane, $C_2$ components and heavier hydrocarbons into a volatile residue gas fraction containing a major portion of said methane and a relatively less volatile fraction containing a major portion of said $C_2$ components and heavier components, in said apparatus there being (a) a first cooling means to cool said gas under pressure connected to provide a cooled stream under pressure;

(b) a first expansion means connected to receive at least a portion of said cooled stream under pressure and to expand it to a lower pressure, whereby said stream is further cooled; and (c) a distillation column connected to said first expansion means to receive the further cooled stream therefrom;

the improvement wherein said apparatus includes (1) first to cool said feed gas under pressure sufficiently to partially condense it;

(2) first separation means connected to said first cooling means to receive said partially condensed feed and to separate it into a vapor and a condensed stream;

(3) dividing means connected to said first separation means to receive said vapor and to divide said vapor into first and second streams;

(4) combining means connected to combine said condensed stream and said first stream into a combined stream;

(5) second cooling means connected to said combining means to receive said combined stream and to cool it sufficiently to substantially condense it;

(6) second expansion means connected to said second cooling means to receive said substantially condensed combined stream and to expand it to a pressure below the fractionation pressure;

(7) heat exchange means connected to said second expansion means to receive said expanded combined stream and to heat it, said heat exchange means being further connected to said distillation column at a point to receive a distillation stream rising from fractionation stages of the distillation column and to cool and partially condense said distillation stream; said heat exchange means being further connected to second and third separation means;

(8) said second separation means being connected to said heat exchange means to receive said combined stream and to separate it into a cold vapor stream and a liquid stream, said second separation means being further connected to (a) pumping means and (b) compressing means;

(9) said pumping means being further connected to said distillation column at a first mid-column feed position to supply said liquid stream to said distillation column;

(10) said compressing means being further connected to said distillation column at a second mid-column feed position to supply said cold vapor stream to said distillation column;

(11) said third separation means being connected to said heat exchange means to receive said partially condensed distillation stream and to separate it into said volatile residue gas fraction and a reflux stream, said third separation means being further connected to said distillation column to supply said reflux stream to the distillation column at a top column feed position;

(12) first expansion means being connected to said dividing means to receive said second stream and expand it to said lower pressure, said first expansion means being further connected to said distillation column to supply said expanded stream to said column at a third mid-column feed position; and

(13) control means adapted to regulate the temperatures of said combined stream, said second stream and said reflux stream to maintain column overhead temperature at a temperature whereby the major portion of said $C_2$ components and heavier components is recovered in said relatively less volatile fraction.

31. In an apparatus for the separation of a feed gas containing methane, $C_2$ components and heavier hydrocarbon components into a volatile residue gas fraction containing a major portion of said methane and a relatively less volatile fraction containing a major portion of said $C_2$ components and heavier components; in said apparatus there being (a) a first cooling means to cool said gas under pressure connected to provide a cooled stream under pressure;

(b) a first expansion means connected to receive at least a portion of said cooled stream under pressure and to expand it to a lower pressure, whereby said stream is further cooled; and (c) a distillation column connected to said expansion means to receive the further cooled stream therefrom;

the improvement wherein said apparatus includes (1) dividing means prior to said first cooling means to divide said feed gas into a first gaseous stream and a second gaseous stream;

(2) second cooling means connected to said dividing means to receive said first stream and to cool it sufficiently to substantially condense it;

(3) second expansion means connected to said second cooling means to receive the substantially condensed first stream therefrom and to expand it to a pressure below the fractionation pressure;

(4) heat exchange means connected to said second expansion means to receive said expanded first stream and to heat it, said heat exchange means being further connected to said distillation column at a point to receive a distillation stream rising from fractionation stages of the distillation column wherein said heat exchange means cools and partially condenses said distillation stream;; said heat exchange means being further connected to first and second separation means;

(5) said first separation means being connected to said heat exchange means to receive said first stream and to separate it into a cold vapor stream and a liquid stream, said first separation means being further connected to (a) pumping means and (b) compressing means;

(6) said pumping means being further connected to said distillation column at a first mid-column feed position to supply said liquid stream to said distillation column;

(7) said compressing means being further connected to said distillation column at a second mid-column feed position to supply said cold vapor stream to said distillation column;

(8) said second separation means being connected to said heat exchange means to receive said partially condensed distillation stream and to separate it into said volatile residue gas fraction and a reflux stream, said second separation means being further connected to said distillation column to supply said reflux stream to the distillation column at a top column feed position;

(9) said first cooling means being connected to said dividing means to receive said second stream and to cool it;

(10) said first expansion means being connected to said first cooling means to receive said cooled second stream and to expand and further cool it; said first expansion means being further connected to said distillation column to supply said second stream to the column at a third mid-column feed position; and

(11) control means adapted to regulate the temperatures of said first stream, said second stream and said reflux stream to maintain column overhead temperature at a temperature whereby the major portion of said $C_2$ components and heavier components is recovered in said relatively less volatile fraction.

32. In an apparatus for the separation of a gas containing methane, $C_2$ components and heavier hydrocarbon components into a volatile residue gas fraction containing a major portion of said methane and a relatively less volatile fraction containing a major portion of said $C_2$ components and heavier components; in said apparatus there being (a) a first cooling means to cool said gas under pressure connected to provide a cooled stream under pressure;

(b) a first expansion means connected to receive at least a portion of said cooled stream under pressure and to expand it to a lower pressure, whereby said stream is further cooled; and (c) a distillation column connected to said expansion means to receive the further cooled stream therefrom;

the improvement wherein said apparatus includes (1) dividing means after said first cooling means to divide said cooled stream into a first stream and a second stream;

(2) second cooling means connected to said dividing means to receive said first stream and to cool it sufficiently to substantially condense it;

(3) second expansion means connected to said second cooling means to receive the substantially condensed first stream therefrom and to expand it to a pressure below the fractionation pressure;

(4) heat exchange means connected to said second expansion means to receive said expanded first stream and to heat it, said heat exchange means being further connected to said distillation column at a point to receive a distillation stream rising from fractionation stages of the distillation column wherein said heat exchange means cools and partially condenses said distillation stream; said heat exchange means being further connected to first and second separation means;

(5) said first separation means being connected to said heat exchange means to receive said first stream and to separate it into a cold vapor stream and a liquid stream, said first separation means being further connected to (a) pumping means and (b) compressing means;

(6) said pumping means being further connected to said distillation column at a first mid-column feed position to supply said liquid stream to said distillation column;

(7) said compressing means being further connected to said distillation column at a second mid-column feed position to supply said cold vapor stream to said distillation column;

(8) said second separation means being connected to said heat exchange means to receive said partially condensed distillation stream and to separate it into said volatile residue gas fraction and a reflux stream, said second separation means being further connected to said distillation column to supply said reflux stream to the distillation column at a top column feed position;

(9) said first expansion means being connected to said dividing means to receive said second stream and to expand and cool it; said first expansion means being further connected to said distillation column to supply said second stream to the column at a third mid-column feed position; and

(10) control means adapted to regulate the temperatures of said first stream, said second stream and said reflux stream to maintain column overhead temperature at a temperature whereby the major portion of said $C_2$ components and heavier components is recovered in said relatively less volatile fraction.

33. The improvement according to claim 30, 31 or 32 wherein the distillation column is a lower portion of a fractionation tower and wherein the heat exchange means is positioned in a portion of the tower above the distillation column.

34. The improvement according to claim 30, 31 or 32 wherein a dephlegmator is connected to said second expansion means to receive the expanded stream and to provide for the heating of said expanded stream, said dephlegmator being further connected to said distillation column at a point to (i) receive a distillation stream rising from fractionation stages of the distillation column whereby said expanded stream cools and partially condenses said distillation stream as said expanded stream is heated and whereby said partially condensed distillation stream is separated to provide said volatile residue gas and said reflux stream and;

(ii) supply the reflux stream formed in the dephlegmator to the top fractionation stage of the distillation column; and wherein said dephlegmator is further connected to separation means; said separation means being connected to said dephlegmator to receive said heated expanded stream and to separate it into said cold vapor stream and said liquid stream, said separation means being further connected to (a) said pumping means and (b) said compressing means.

35. The improvement according to claim 30, 31 or 32 wherein said apparatus includes another heat exchange means connected to receive said compressed cold vapor stream and to cool it, said other heat exchange means being further connected to said column to supply said cooled compressed stream to said column at a mid-column feed position.

* * * * *

UNITED STATES PATENT AND TRADEMARK OFFICE
CERTIFICATE OF CORRECTION

PATENT NO. : 4,869,740

DATED : September 26, 1989

INVENTOR(S) : Campbell et al.

It is certified that error appears in the above-identified patent and that said Letters Patent is hereby corrected as shown below:

Col. 16, line 19, "of at" should read --of at least--;

Col. 16, line 25, "of least" should read --of at least--;

Col. 18, line 14, after "first" insert --cooling means adapted--.

Signed and Sealed this

Fourth Day of September, 1990

Attest:

HARRY F. MANBECK, JR.

Attesting Officer

Commissioner of Patents and Trademarks